United States Patent [19]

Kurfuerst et al.

[11] Patent Number: 5,663,141
[45] Date of Patent: Sep. 2, 1997

[54] HIRUDIN/POLYALKYLENE GLYCOL CONJUGATES AND HIRUDIN MUTEINS

[75] Inventors: Manfred Kurfuerst, Hassloch; Klaus Ruebsamen, Neustadt; Bernhard Schmied, Frankenthal; Wolfgang Koerwer, Gruenstadt; Juergen Schweden, Deidesheim; Hans Wolfgang Hoeffken, Ludwigshafen, all of Germany

[73] Assignee: BASF Aktiengesellschaft, Ludwigshafen, Germany

[21] Appl. No.: 859,453

[22] PCT Filed: Nov. 22, 1990

[86] PCT No.: PCT/EP90/01998

§ 371 Date: May 29, 1992

§ 102(e) Date: May 29, 1992

[87] PCT Pub. No.: WO91/08229

PCT Pub. Date: Jun. 13, 1991

[30] Foreign Application Priority Data

Dec. 1, 1989 [DE] Germany ............... 39 39 800.5

[51] Int. Cl.$^6$ .............. A61K 38/58; C07K 14/815; C07K 17/00
[52] U.S. Cl. .............. 514/12; 514/21; 514/2; 530/324; 530/403; 530/402; 530/858
[58] Field of Search .............. 530/402, 403, 530/324, 858; 514/12, 21, 2

[56] References Cited

FOREIGN PATENT DOCUMENTS 0236987 9/1987 European Pat. Off. .
345 616 12/1989 European Pat. Off. .

OTHER PUBLICATIONS

Matsushima et al. Modification of E. coli asparaginese. Chem Lett. (1980), 773.
Abuchowski et al. Treatment of L51784 Tumor Bearing BDF Mice. Cancer Treat. Rep (1979) 63:1127.
Chen et al. Properties of Two Urate Oxidases Biochem Biophys Acta (1981) 660: 293–298.
Walsmann et al. Hirudin Binding to Soluble Dextran. J. Biol Chem (1977) 252: 3582.
Fortkamp et al. Cloning and Expression in E. coli of a Synthetic DNA for Hirodin DNA (1986) 5:511.
Wallace et al. Contribution of the N-terminal Region of Hirudin to Its Interaction with Thrombin Biochemistry (1989) 28: 10079.
Riehl–Bellon et al. Purification and Biochemical Characterization of Recombinant Hirudin. Biochemistry (1989) 28: 2941.
Chang. The Functional Domain of Hirudin FEBS–Letters (1983) 164: 307.
Dodt et al. Interaction of Sole Specific Hirudin Variants with α–Thrombin FEBS Lett. (1988) 229: 87.
Braun et al. use of Site–Directed Mutagenesis to Investigate the Basis for the Specificity of Hirudin. Biochem. (1988) 27:6517.
Tripies. Hirudin: a Family of Iso–Proteins–Isolation and Sequence Determination of New Hirudins. Folia Haematol (1988) 115:30.
Dodt et al. The Complete Covalent Structure of Hirudin. Biol Chem (1985) 366:379.
Bowie et al. Science 247:1306–1310 Mar. 1990.
Lehringer, A.L. "Biochemistry", published by Worth Publishers, Inc. 1970 (see p. 113).
Walsmann et al., "Hirudin binding to soluble dextran", 1989, pp. 72–74, Pharmazie, vol. 44.

Primary Examiner—Anthony C. Caputa
Attorney, Agent, or Firm—Keil & Weinkauf

[57] ABSTRACT

Hirudin/polyalkylene glycol derivatives of the formula $$[A-(CH_2)_n-[O-(CH_2)_{nlm}-B-]_p \text{Hir [sic]}] \quad I$$

and hirudin muteins and the preparation thereof are described. The compounds are suitable for controlling diseases.

15 Claims, 5 Drawing Sheets

FIG. 2A

Synthetic DNA fragments used:

Fragment 1A:

```
aat tca atc gat act atg gtt tac act gac tgc act gaa tcc ggt cag aac ctg tgc
    gt tag cta tga tac caa atg tga ctg acg tga ctt agg cca gtc ttg gac acg
       Met Val Tyr Thr Asp Cys Thr Glu Ser Gly Gln Asn Leu Cys
                     1                 5                    10 ctg tgc gaa ggc tct aac gtt tgc ggc cag ggc
gac acg ctt ccg aga ttg caa a
Leu Cys Glu Gly Ser Asn Val(Cys Gly Gln Gly)
15                  20              25
```

Fragment 2A:

```
    aac aaa tgc atc ctg tct gac ggc gaa ctt ttt aaa aac cag tgc gtt act ggc gaa ggt ac
cg ccg gtc ccg ttg tag acg aga ctg ccg ctt gaa aaa ttt ttg gtc acg caa tga cct c
(Gly Gln Gly)Asn Lys Cys Ile Leu Ser Asp Gly Glu Leu Phe Lys Asn Gln Cys Val Thr Gly Glu(Gly)
       25                  30                  35                  40
```

Fragment 2B:

```
    aac aaa tgc atc ctg ggc aaa ttt tgg cag aaa ttt ttg aac cag tgc gtt act ggc gaa ggt ac
cg ccg gtc ccg ttg tag acg tag cct ttt aaa acg gtc ttt aaa aac ttg gtc acg caa tga cct c
(Gly Gln Gly)Asn Lys Cys Ile Leu Gly Lys Phe Trp Gln Lys Phe Leu Asn Gln Cys Val Thr Gly Glu(Gly)
       25                  30                  35                  40
```

Fragment 2C:

```
    aac aaa tgc atc ctg tct aga ggc tct aaa ttt ttg aac cag tgc gtt act ggc gaa ggt ac
cg ccg gtc ccg ttg tag acg tag gac aga tct ccg aga ttt aaa aac ttg gtc acg caa tga cct c
(Gly Gln Gly)Asn Lys Cys Ile Leu Ser Arg Gly Ser Lys Phe Leu Asn Gln Cys Val Thr Gly Glu(Gly)
       25                  30                  35                  40
```

Fragment 2D:

```
    aac aaa tgc atc ctg tct aga ggc tct aaa ttt aac cgt gca aac cag tgc gtt act ggc gaa ggt ac
cg ccg gtc ccg ttg tag acg tag gac aga tct ccg aga ttt ttg gca cgt ttg gtc acg caa tga cct c
(Gly Gln Gly)Asn Lys Cys Ile Leu Ser Arg Gly Ser Lys Phe Asn Arg Ala Asn Gln Cys Val Thr Gly Glu(Gly)
       25                  30                  35                  40
```

Fragment 3A:

```
   c  ccg aaa ccg cag tct cac aac gac ggc gac ttc gaa gaa atc ccg gaa gaa tac ctg cag taa tag g
ca tgg ttt ggc gtc aga gtg ttg ctg ccg ctg aag ctt ctt tag ggc ctt ctt atg gac gtc att atc cag ct
(Thr)Pro Lys Pro Gln Ser His Asn Asp Gly Asp Phe Glu Glu Ile Pro Glu Glu Tyr Leu Gln End End
    45              50              55              60              65
```

Fragment 3B:

```
   c  ccg cgt ccg cag tct cac aac gac ggc gac ttc gaa gaa atc ccg gaa gaa tac ctg cag taa tag g
ca tgg gca gca gtc aga gtg ttg ctg ccg ctg aag ctt ctt tag ggc ctt ctt atg gac gtc att atc cag ct
(Thr)Pro Arg Pro Gln Ser His Asn Asp Gly Asp Phe Glu Glu Ile Pro Glu Glu Tyr Leu Gln End End
    45              50              55              60              65
```

Fragment 3C:

```
   ca ccg cag ccg cag tct cac aac gac ggc gac ttc gaa gaa atc ccg gaa gaa tac ctg cag taa tag g
ca tgg ggc gtc gtc aga gtg ttg ctg ccg ctg aag ctt ctt tag ggc ctt ctt atg gac gtc att atc cag ct
(Thr)Pro Gln Pro Gln Ser His Asn Asp Gly Asp Phe Glu Glu Ile Pro Glu Glu Tyr Leu Gln End End
    45              50              55              60              65
```

FIG. 2B

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 61 amino acids
        ( B ) TYPE: amino acid
        ( C ) TOPOLOGY: unknown ( i i ) MOLECULE TYPE: peptide ( i x ) FEATURE:
        ( D ) OTHER INFORMATION: Xaa-Xaa at positions 1 and 2 can
        be Val-Val, Ile-Thr, Leu-Thr or Pro-Val; Xaa at position
        24 can be Gln or Glu; Xaa at position 27 can be Lys, Arg
        or Asn; Xaa at position 43 can be Lys, Arg, Asn or Gln;
        Xaa at position 54 can be Glu or Pro; Xaa at position 61
        can be Asp or Gln.

( x i ) SEQUENCE DESCRIPTION: SEQ ID NO: 1:

```
Xaa Xaa Tyr Thr Asp Cys Thr Glu Ser Gly Gln Asn Leu Cys Leu Cys
 1           5                   10                  15

Glu Gly Ser Asn Val Cys Gly Xaa Gly Asn Xaa Cys Ile Leu Lys Gly
            20              25                  30

Asn Gln Cys Val Thr Gly Glu Gly Thr Pro Xaa Pro Gln Ser His Asn
        35              40              45

Asp Gly Asp Phe Glu Xaa Ile Pro Glu Glu Tyr Leu Xaa
        50              55              60
```

( 2 ) INFORMATION FOR SEQ ID NO: 2:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO: 2:

```
CCG GGG AAT TCC CGG GGA TCC GTC GAC CTG CAG                    33
Pro Gly Asn Ser Arg Gly Ser Val Asp Leu Gln
 1           5                   10
```

( 2 ) INFORMATION FOR SEQ ID NO: 3:

( i ) SEQUENCE CHARACTERISTICS:
        ( A ) LENGTH: 93 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO: 3:

```
AATTCAATCG ATACT ATG GTT GTT TAC ACT GAC TGC ACT GAA TCC GGT CAG   51
               Met Val Val Tyr Thr Asp Cys Thr Glu Ser Gly Gln
                1           5                   10

AAC CTG TGC CTG TGC GAA GGC TCT AAC GTT TGC GGC CAG GGC            93
Asn Leu Cys Leu Cys Glu Gly Ser Asn Val Cys Gly Gln Gly
            15              20              25
```

( 2 ) INFORMATION FOR SEQ ID NO: 4:

( i ) SEQUENCE CHARACTERISTICS:
        ( A ) LENGTH: 78 base pairs
        ( B ) TYPE: nucleic acid
        ( C ) STRANDEDNESS: unknown (D) TOPOLOGY: unknown (xi) SEQUENCE DESCRIPTION: SEQ ID NO: 4:

```
GTTAGCTA TGA TAC CAA CAA ATG TGA CTG ACG TGA CTT AGG CCA GTC        47
         Met Val Val Tyr Thr Asp Cys Thr Glu Ser Gly Gln
         1           5                   10

TTG GAC ACG GAC ACG CTT CCG AGA TTG CAA A                          78
Asn Leu Cys Leu Cys Glu Gly Ser Asn Val
        15                  20
```

(2) INFORMATION FOR SEQ ID NO: 5:

(i) SEQUENCE CHARACTERISTICS:
        (A) LENGTH: 59 base pairs
        (B) TYPE: nucleic acid
        (C) STRANDEDNESS: unknown
        (D) TOPOLOGY: unknown (xi) SEQUENCE DESCRIPTION: SEQ ID NO: 5:

```
AAC AAA TGC ATC CTG GGC TCT GAC GGC GAA AAA AAC CAG TGC GTT        45
Asn Lys Cys Ile Leu Gly Ser Asp Gly Glu Lys Asn Gln Cys Val
1            5                   10                  15

ACT GGC GAA GGT AC                                                 59
Thr Gly Glu Gly
```

(2) INFORMATION FOR SEQ ID NO: 6:

(i) SEQUENCE CHARACTERISTICS:
        (A) LENGTH: 66 base pairs
        (B) TYPE: nucleic acid
        (C) STRANDEDNESS: unknown
        (D) TOPOLOGY: unknown (xi) SEQUENCE DESCRIPTION: SEQ ID NO: 6:

```
CG CCG GTC CCG TTG TTT ACG TAG GAC CCG AGA CTG CCG CTT TTT         44
   Gly Gln Gly Asn Lys Cys Ile Leu Gly Ser Asp Gly Glu Lys
   1           5                   10

TTG GTC ACG CAA TGA CCG CTT C                                      66
Asn Gln Cys Val Thr Gly Glu
15                  20
```

(2) INFORMATION FOR SEQ ID NO: 7:

(i) SEQUENCE CHARACTERISTICS:
        (A) LENGTH: 59 base pairs
        (B) TYPE: nucleic acid
        (C) STRANDEDNESS: unknown
        (D) TOPOLOGY: unknown (xi) SEQUENCE DESCRIPTION: SEQ ID NO: 7:

```
AAC AAA TGC ATC CTG GGC AAA AAC GGC CAG AAA AAC CAG TGC GTT ACT    48
Asn Lys Cys Ile Leu Gly Lys Asn Gly Gln Lys Asn Gln Cys Val Thr
1            5                   10                  15

GGC GAA GGT AC                                                     59
Gly Glu Gly
```

(2) INFORMATION FOR SEQ ID NO: 8:

(i) SEQUENCE CHARACTERISTICS:
        (A) LENGTH: 66 base pairs
        (B) TYPE: nucleic acid
        (C) STRANDEDNESS: unknown
        (D) TOPOLOGY: unknown (xi) SEQUENCE DESCRIPTION: SEQ ID NO: 8:

```
CG CCG GTC CCG TTG TTT ACG TAG GAC CCG TTT TTG CCG GTC TTT TTG     47
   Gly Gln Gly Asn Lys Cys Ile Leu Gly Lys Asn Gly Gln Lys Asn
```

( 2 ) INFORMATION FOR SEQ ID NO: 9:

( i ) SEQUENCE CHARACTERISTICS:
    ( A ) LENGTH: 59 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO: 9:

```
          1                   5                    10                   15
AAC  AAA  TGC  ATC  CTG  GGC  TCT  AAA  GGC  CAG  AAA  AAC  CAG  TGC  GTT  ACT    48
Asn  Lys  Cys  Ile  Leu  Gly  Ser  Lys  Gly  Gln  Lys  Asn  Gln  Cys  Val  Thr
 1                   5                    10                   15

GGC  GAA  GGT  AC                                                                 59
Gly  Glu  Gly
```

( 2 ) INFORMATION FOR SEQ ID NO: 10:

( i ) SEQUENCE CHARACTERISTICS:
    ( A ) LENGTH: 66 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO: 10:

```
CG   CCG  GTC  CCG  TTG  TTT  ACG  TAG  GAC  CCG  AGA  TTT  CCG  GTC  TTT  TTG    47
     Gly  Gln  Gly  Asn  Lys  Cys  Ile  Leu  Gly  Ser  Lys  Gly  Gln  Lys  Asn
      1                   5                    10                   15

GTC  ACG  CAA  TGA  CCG  CTT  C                                                   66
Gln  Cys  Val  Thr  Gly  Glu
                     20
```

( 2 ) INFORMATION FOR SEQ ID NO: 11:

( i ) SEQUENCE CHARACTERISTICS:
    ( A ) LENGTH: 59 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO: 11:

```
AAC  AAA  TGC  ATC  CTG  GGC  TCT  AAA  GGC  GAA  CGT  AAC  CAG  TGC  GTT  ACT    48
Asn  Lys  Cys  Ile  Leu  Gly  Ser  Lys  Gly  Glu  Arg  Asn  Gln  Cys  Val  Thr
 1                   5                    10                   15

GGC  GAA  GGT  AC                                                                 59
Gly  Glu  Gly
```

( 2 ) INFORMATION FOR SEQ ID NO: 12:

( i ) SEQUENCE CHARACTERISTICS:
    ( A ) LENGTH: 66 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO: 12:

```
CG   CCG  GTC  CCG  TTG  TTT  ACG  TAG  GAC  CCG  AGA  TTT  CCG  CTT  GCA  TTG    47
     Gly  Gln  Gly  Asn  Lys  Cys  Ile  Leu  Gly  Ser  Lys  Gly  Glu  Arg  Asn
      1                   5                    10                   15

GTC  ACG  CAA  TGA  CCG  CTT  C                                                   66
Gln  Cys  Val  Thr  Gly  Glu
                     20
```

(2) INFORMATION FOR SEQ ID NO: 13:

(i) SEQUENCE CHARACTERISTICS:
(A) LENGTH: 68 base pairs
(B) TYPE: nucleic acid
(C) STRANDEDNESS: unknown
(D) TOPOLOGY: unknown (xi) SEQUENCE DESCRIPTION: SEQ ID NO: 13:

```
C  CCG  AAA  CCG  CAG  TCT  CAC  AAC  GAC  GGC  GAC  TTC  GAA  GAA  ATC  CCG        46
   Pro  Lys  Pro  Gln  Ser  His  Asn  Asp  Gly  Asp  Phe  Glu  Glu  Ile  Pro
   1                 5                      10                          15

GAA  GAA  TAC  CTG  CAG  TAA  TAG  G                                                 68
Glu  Glu  Tyr  Leu  Gln  Xaa  Xaa
                    20
```

(2) INFORMATION FOR SEQ ID NO: 14:

(i) SEQUENCE CHARACTERISTICS:
(A) LENGTH: 76 base pairs
(B) TYPE: nucleic acid
(C) STRANDEDNESS: unknown
(D) TOPOLOGY: unknown (xi) SEQUENCE DESCRIPTION: SEQ ID NO: 14:

```
CA  TGG  GGC  TTT  GGC  GTC  AGA  GTG  TTG  CTG  CCG  CTG  AAG  CTT  CTT  TAG       47
    Thr  Pro  Lys  Pro  Gln  Ser  His  Asn  Asp  Gly  Asp  Phe  Glu  Glu  Ile
    1                  5                       10                         15

GGC  CTT  CTT  ATG  GAC  GTC  ATT  ATC  CAG  CT                                      76
Pro  Glu  Glu  Tyr  Leu  Gln  Xaa  Xaa
                         20
```

(2) INFORMATION FOR SEQ ID NO: 15:

(i) SEQUENCE CHARACTERISTICS:
(A) LENGTH: 68 base pairs
(B) TYPE: nucleic acid
(C) STRANDEDNESS: unknown
(D) TOPOLOGY: unknown (xi) SEQUENCE DESCRIPTION: SEQ ID NO: 15:

```
C  CCG  CGT  CCG  CAG  TCT  CAC  AAC  GAC  GGC  GAC  TTC  GAA  GAA  ATC  CCG        46
   Pro  Arg  Pro  Gln  Ser  His  Asn  Asp  Gly  Asp  Phe  Glu  Glu  Ile  Pro
   1                 5                      10                          15

GAA  GAA  TAC  CTG  CAG  TAA  TAG  G                                                 68
Glu  Glu  Tyr  Leu  Gln  Xaa  Xaa
                    20
```

(2) INFORMATION FOR SEQ ID NO: 16:

(i) SEQUENCE CHARACTERISTICS:
(A) LENGTH: 76 base pairs
(B) TYPE: nucleic acid
(C) STRANDEDNESS: unknown
(D) TOPOLOGY: unknown (xi) SEQUENCE DESCRIPTION: SEQ ID NO: 16:

```
CA  TGG  GGC  GCA  GGC  GTC  AGA  GTG  TTG  CTG  CCG  CTG  AAG  CTT  CTT  TAG       47
    Thr  Pro  Arg  Pro  Gln  Ser  His  Asn  Asp  Gly  Asp  Phe  Glu  Glu  Ile
    1                  5                       10                         15

GGC  CTT  CTT  ATG  GAC  GTC  ATT  ATC  CAG  CT                                      76
Pro  Glu  Glu  Tyr  Leu  Gln  Xaa  Xaa
                         20
```

(2) INFORMATION FOR SEQ ID NO: 17:

(i) SEQUENCE CHARACTERISTICS:

( A ) LENGTH: 68 base pairs
( B ) TYPE: nucleic acid
( C ) STRANDEDNESS: unknown
( D ) TOPOLOGY: unknown ( x i ) SEQUENCE DESCRIPTION: SEQ ID NO: 17:

```
C  CCG CAG CCG CAG TCT CAC AAC GAC GGC GAC TTC GAA GAA ATC CCG    46
   Pro Gln Pro Gln Ser His Asn Asp Gly Asp Phe Glu Glu Ile Pro
   1               5                   10                  15

GAA GAA TAC CTG CAG TAA TAG G                                     68
Glu Glu Tyr Leu Gln Xaa Xaa
            20
```

( 2 ) INFORMATION FOR SEQ ID NO: 18:

( i ) SEQUENCE CHARACTERISTICS:
( A ) LENGTH: 76 base pairs
( B ) TYPE: nucleic acid
( C ) STRANDEDNESS: unknown
( D ) TOPOLOGY: unknown ( x i ) SEQUENCE DESCRIPTION: SEQ ID NO: 18:

```
CA TGG GGC GTC GGC GTC AGA GTG TTG CTG CCG CTG AAG CTT CTT TAG    47
   Thr Pro Gln Pro Gln Ser His Asn Asp Gly Asp Phe Glu Glu Ile
   1               5                   10                  15

GGC CTT CTT ATG GAC GTC ATT ATC CAG CT                            76
Pro Glu Glu Tyr Leu Gln Xaa Xaa
            20
```

( 2 ) INFORMATION FOR SEQ ID NO: 19:

( i ) SEQUENCE CHARACTERISTICS:
( A ) LENGTH: 65 amino acids
( B ) TYPE: amino acid
( D ) TOPOLOGY: unknown ( i i ) MOLECULE TYPE: peptide ( x i ) SEQUENCE DESCRIPTION: SEQ ID NO: 19:

```
Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Lys
                20                  25                  30

Asn Gly Gln Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
        50                  55                  60

Gln
65
```

( 2 ) INFORMATION FOR SEQ ID NO: 20:

( i ) SEQUENCE CHARACTERISTICS:
( A ) LENGTH: 65 amino acids
( B ) TYPE: amino acid
( D ) TOPOLOGY: unknown ( i i ) MOLECULE TYPE: peptide ( x i ) SEQUENCE DESCRIPTION: SEQ ID NO: 20:

```
Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
                20                  25                  30

Lys Gly Gln Lys Asn Gln Cys Val Thr Gly Glu Gly Thr Pro Lys Pro
```

```
                              35                          40                          45
Gln  Ser  His  Asn  Asp  Gly  Asp  Phe  Glu  Glu  Ile  Pro  Glu  Glu  Tyr  Leu
          50                            55                       60

Gln
65
```

( 2 ) INFORMATION FOR SEQ ID NO: 21:

( i ) SEQUENCE CHARACTERISTICS:
        ( A ) LENGTH: 65 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 21:

```
Val  Val  Tyr  Thr  Asp  Cys  Thr  Glu  Ser  Gly  Gln  Asn  Leu  Cys  Leu  Cys
1                        5                        10                       15

Glu  Gly  Ser  Asn  Val  Cys  Gly  Gln  Gly  Asn  Lys  Cys  Ile  Leu  Gly  Lys
               20                       25                       30

Asn  Gly  Glu  Arg  Asn  Gln  Cys  Val  Thr  Gly  Glu  Gly  Thr  Pro  Lys  Pro
          35                       40                       45

Gln  Ser  His  Asn  Asp  Gly  Asp  Phe  Glu  Glu  Ile  Pro  Glu  Glu  Tyr  Leu
     50                            55                       60

Gln
65
```

( 2 ) INFORMATION FOR SEQ ID NO: 22:

( i ) SEQUENCE CHARACTERISTICS:
        ( A ) LENGTH: 65 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO: 22:

```
Val  Val  Tyr  Thr  Asp  Cys  Thr  Glu  Ser  Gly  Gln  Asn  Leu  Cys  Leu  Cys
1                        5                        10                       15

Glu  Gly  Ser  Asn  Val  Cys  Gly  Gln  Gly  Asn  Lys  Cys  Ile  Leu  Gly  Ser
               20                       25                       30

Lys  Gly  Glu  Arg  Asn  Gln  Cys  Val  Thr  Gly  Glu  Gly  Thr  Pro  Arg  Pro
          35                       40                       45

Gln  Ser  His  Asn  Asp  Gly  Asp  Phe  Glu  Glu  Ile  Pro  Glu  Glu  Tyr  Leu
     50                            55                       60

Gln
65
```

( 2 ) INFORMATION FOR SEQ ID NO: 23:

( i ) SEQUENCE CHARACTERISTICS:
        ( A ) LENGTH: 65 amino acids
        ( B ) TYPE: amino acid
        ( D ) TOPOLOGY: unknown ( x i ) SEQUENCE DESCRIPTION: SEQ ID NO: 23:

```
Val  Val  Tyr  Thr  Asp  Cys  Thr  Glu  Ser  Gly  Gln  Asn  Leu  Cys  Leu  Cys
1                        5                        10                       15

Glu  Gly  Ser  Asn  Val  Cys  Gly  Gln  Gly  Asn  Lys  Cys  Ile  Leu  Gly  Lys
               20                       25                       30

Asn  Gly  Gln  Lys  Asn  Gln  Cys  Val  Thr  Gly  Glu  Gly  Thr  Pro  Gln  Pro
          35                       40                       45
```

```
Gln  Ser  His  Asn  Asp  Gly  Asp  Phe  Glu  Glu  Ile  Pro  Glu  Glu  Tyr  Leu
         50                      55                      60

Gln
65
```

( 2 ) INFORMATION FOR SEQ ID NO: 24:

( i ) SEQUENCE CHARACTERISTICS:
    ( A ) LENGTH: 65 amino acids
    ( B ) TYPE: amino acid
    ( C ) TOPOLOGY: unknown ( i i ) MOLECULE TYPE: peptide ( i x ) FEATURE:
    ( D ) OTHER INFORMATION: Xaa-Xaa at positions 1 and 2 can
    be Val-Val, Ile-Thr, Leu-Thr or Pro-Val; Xaa at position
    24 can be Gln or Glu; Xaa at position 27 can be Lys, Arg
    or Asn; Xaa at position 32 can be Ser or Lys; Xaa at
    position 33 can be Asp, Lys or Asn; Xaa at position 35
    can be Glu or Gln; Xaa at position 36 can be Lys, Arg or
    Asn; Xaa at position 47 can be Lys, Arg, Asn or Gln; Xaa
    at position 58 can be Glu or Pro; Xaa at position 65 can
    be Asp or Gln.

( x i ) SEQUENCE DESCRIPTION: SEQ ID NO: 24:

```
Xaa  Xaa  Tyr  Thr  Asp  Cys  Thr  Glu  Ser  Gly  Gln  Asn  Leu  Cys  Leu  Cys
1                        5                        10                       15

Glu  Gly  Ser  Asn  Val  Cys  Gly  Xaa  Gly  Asn  Xaa  Cys  Ile  Leu  Gly  Xaa
              20                       25                       30

Xaa  Gly  Xaa  Xaa  Asn  Gln  Cys  Val  Thr  Gly  Glu  Gly  Thr  Pro  Xaa  Pro
         35                       40                       45

Gln  Ser  His  Asn  Asp  Gly  Asp  Phe  Glu  Xaa  Ile  Pro  Glu  Glu  Tyr  Leu
         50                      55                      60

Xaa
65
```

( 2 ) INFORMATION FOR SEQ ID NO: 25:

( i ) SEQUENCE CHARACTERISTICS:
    ( A ) LENGTH: 64 amino acids
    ( B ) TYPE: amino acid
    ( C ) TOPOLOGY: unknown ( i i ) MOLECULE TYPE: peptide ( i x ) FEATURE:
    ( D ) OTHER INFORMATION: Xaa-Xaa at positions 1 and 2 can
    be Val-Val, Ile-Thr, Leu-Thr or Pro-Val; Xaa at position
    24 can be Gln or Glu; Xaa at position 27 can be Lys, Arg
    or Asn; Xaa at position 32 can be Asp, Lys or Asn; Xaa
    at position 34 can be Glu or Gln; Xaa at position 35 can
    be Lys, Arg or Asn; Xaa at position 46 can be Lys, Arg,
    Asn or Gln; Xaa at position 57 can be Glu or Pro; Xaa at
    position 64 can be Asp or Gln.

( x i ) SEQUENCE DESCRIPTION: SEQ ID NO: 25:

```
Xaa  Xaa  Tyr  Thr  Asp  Cys  Thr  Glu  Ser  Gly  Gln  Asn  Leu  Cys  Leu  Cys
1                        5                        10                       15

Glu  Gly  Ser  Asn  Val  Cys  Gly  Xaa  Gly  Asn  Xaa  Cys  Ile  Leu  Gly  Xaa
              20                       25                       30

Gly  Xaa  Xaa  Asn  Gln  Cys  Val  Thr  Gly  Glu  Gly  Thr  Pro  Xaa  Pro  Gln
         35                       40                       45

Ser  His  Asn  Asp  Gly  Asp  Phe  Glu  Xaa  Ile  Pro  Glu  Glu  Tyr  Leu  Xaa
         50                      55                      60
```

( 2 ) INFORMATION FOR SEQ ID NO: 26:

( i ) SEQUENCE CHARACTERISTICS:
        ( A ) LENGTH: 64 amino acids
        ( B ) TYPE: amino acid
        ( C ) TOPOLOGY: unknown ( i i ) MOLECULE TYPE: peptide ( i x ) FEATURE:
        ( D ) OTHER INFORMATION: Xaa-Xaa at positions 1 and 2 can be
        Val-Val, Ile- Thr, Leu-Thr or Pro-Val; Xaa at position 24
        can be Gln or Glu; Xaa at position 27 can be Lys, Arg or
        Asn; Xaa at position 32 can be Ser or Lys; Xaa at
        position 33 can be Asp, Lys or Asn; Xaa at position 35
        can be Lys, Arg or Asn; Xaa at position 46 can be Lys,
        Arg, Asn or Gln; Xaa at position 57 can be Glu or Pro;
        Xaa at position 64 can be Asp or Gln.

( x i ) SEQUENCE DESCRIPTION: SEQ ID NO: 26:

```
Xaa  Xaa  Tyr  Thr  Asp  Cys  Thr  Glu  Ser  Gly  Gln  Asn  Leu  Cys  Leu  Cys
 1                    5                        10                       15
Glu  Gly  Ser  Asn  Val  Cys  Gly  Xaa  Gly  Asn  Xaa  Cys  Ile  Leu  Gly  Xaa
               20                   25                        30
Xaa  Gly  Xaa  Asn  Gln  Cys  Val  Thr  Gly  Glu  Gly  Thr  Pro  Xaa  Pro  Gln
           35                        40                       45
Ser  His  Asn  Asp  Gly  Asp  Phe  Glu  Xaa  Ile  Pro  Glu  Glu  Tyr  Leu  Xaa
     50                        55                       60
```

( 2 ) INFORMATION FOR SEQ ID NO: 27:

( i ) SEQUENCE CHARACTERISTICS:
        ( A ) LENGTH: 63 amino acids
        ( B ) TYPE: amino acid
        ( C ) TOPOLOGY: unknown ( i i ) MOLECULE TYPE: peptide ( i x ) FEATURE:
        ( D ) OTHER INFORMATION: Xaa-Xaa at positions 1 and 2 can be
        Val-Val, Ile- Thr, Leu-Thr or Pro-Val; Xaa at position 24
        can be Gln or Glu; Xaa at position 27 can be Lys, Arg or
        Asn; Xaa at position 32 can be Asp, Lys, or Asn; Xaa at
        position 34 Lys, Arg or Asn; Xaa at position 45 can be
        Lys, Arg, Asn or Gln; Xaa at position 56 can be Glu or
        Pro; Xaa at position 63 can be Asp or Gln.

( x i ) SEQUENCE DESCRIPTION: SEQ ID NO: 27:

```
Xaa  Xaa  Tyr  Thr  Asp  Cys  Thr  Glu  Ser  Gly  Gln  Asn  Leu  Cys  Leu  Cys
 1                    5                        10                       15
Glu  Gly  Ser  Asn  Val  Cys  Gly  Xaa  Gly  Asn  Xaa  Cys  Ile  Leu  Gly  Xaa
               20                   25                        30
Gly  Xaa  Asn  Gln  Cys  Val  Thr  Gly  Glu  Gly  Thr  Pro  Xaa  Pro  Gln  Ser
      35                        40                       45
His  Asn  Asp  Gly  Asp  Phe  Glu  Xaa  Ile  Pro  Glu  Glu  Tyr  Leu  Xaa
     50                        55                       60
```

( 2 ) INFORMATION FOR SEQ ID NO: 28:

( i ) SEQUENCE CHARACTERISTICS:
        ( A ) LENGTH: 65 amino acids
        ( B ) TYPE: amino acid
        ( D ) TOPOLOGY: unknown ( i i ) MOLECULE TYPE: peptide ( i x ) FEATURE:
        ( D ) OTHER INFORMATION: Xaa-Xaa at positions 1 and 2 can be
        Val-Val, Ile- Thr or Leu-Thr.

( x i ) SEQUENCE DESCRIPTION: SEQ ID NO: 28:

```
Xaa Xaa Tyr Thr Asp Cys Thr Glu Ser Gly Gln Asn Leu Cys Leu Cys
 1           5                      10                  15
Glu Gly Ser Asn Val Cys Gly Gln Gly Asn Lys Cys Ile Leu Gly Ser
            20                  25              30
Lys Gly Glu Arg Asn Gln Cys Val Thr Gly Glu Gly Thr Pro Arg Pro
        35                  40              45
Gln Ser His Asn Asp Gly Asp Phe Glu Glu Ile Pro Glu Glu Tyr Leu
    50                  55              60
Gln
65 .
```

HIRUDIN/POLYALKYLENE GLYCOL CONJUGATES AND HIRUDIN MUTEINS

The present application is the national phase of PCT/EP90/01998, Nov. 22, 1990.

BACKGROUND OF THE INVENTION

The invention relates to novel hirudin muteins and to hirudin/polyalkylene glycol conjugates thereof, to the preparation thereof and to the use thereof both for the prophylaxis and therapy of cardiovascular disorders and for modification of macromolecular carriers.

Hirudin is a naturally occurring protein with anticoagulant properties which has been known for a long time. It is the most potent and most selective thrombin inhibitor yet known (Naturwissenschaften, (1955) 42,537; Hopppe-Seylers Z. f ür Biol. Chemie, (1985) 366, 379). The polypeptide can be isolated from the medical leech *Hirudo medicinalis* and is composed of 65 amino acids, contains three disulfide bridges and is sulfated at position tyrosine 63. In addition, there also exist several naturally occurring isoforms which differ from the original hirudin by amino-acid replacement in various positions (Folia Haematol. (1988), 115, 30). Likewise, variants prepared by genetic engineering are known (Biochemistry (1988), 27, 6517, FEBS-Lett. (1988), 229, 87). Hirudin and various variants can now be obtained by genetic engineering means, the sulfate residue on amino acid Tyr 63 being absent in hirudins prepared by genetic engineering methods (Biochemistry (1989), 28, 2941, DNA (1986), 5, 511). The good physiological tolerability of this coagulation inhibitor has likewise been known for some time (Pharmazie (1981), 10, 653).

Despite its favorable pharmacodynamic properties, hirudin is, by reason of its low half-life in the blood of about 50 min., little suited to long-lasting therapeutic applications. It is known that the half-life of proteins can be extended by conjugation with macro-molecules (J. Biol. Chem. (1977), 252, 3582; Biochim. Biophys. Acta (1981), 660, 293). It is often observed after a derivatization of this type with, for example, polyethylene glycol that there is a significant deterioration in the enzymatic activity, which greatly restricts the utilizability of such modified proteins (Cancer. Treat. Rep. (1979), 63, 1127; Chemistry Lett. (1980), 773). In the case of hirudin, it has recently been shown by Walsmann that it was possible by coupling to dextran to achieve a distinct extension of the half-life from about 50 min. to more than 7 h, although there was a drastic loss of activity (Pharmazie (1989), 44, 72). Therapeutic use of such dextan-hirudins [sic] is, despite the favorable alteration in the half-life, impeded by the very low yield of product, the drastically reduced specific activity and the changes, which are possibly connected therewith, in the pharmacodynamic properties.

Conjugation of proteins to macromolecules is often achieved by reaction of the carboxyl groups of the amino acids aspartic acid or glutamic acid, by reaction of the sulfhydryl group of the amino acid cystein or by reaction of the side-chain amino group of the amino acid lysine in the relevant protein. However, it is often precisely the said amino acids which are essentially important for the function of the relevant protein. The derivatization of a protein may be associated with a change in the physical/chemical or enzymatic properties, even up to inactivation. Hirudin contains several aspartic acid and glutamic acid residues, mainly in the C-terminal region of the molecule. Lysine residues, are located in position 27, 36 and 47 in the hirudin molecule. Furthermore, coupling via the C terminus or the N terminus of the molecule would be conceivable. However, it is known that both the acidic amino acids in the C-terminal region (FEBS. Lett. (1983), 164 307–313) and the basic lysine residues, especially the lysine residue No. 47 which is highly exposed in the molecule, are crucially involved in the interaction of hirudin with the protease thrombin (Biol. Chem. Hoppe-Seyler (1985), 366, 379–385). Reactions at the N terminus, such as, for example, an extension (Biochemistry (1989), 28, 10079) lead to a drastic decrease in the inhibitory activity of hirudin. It was therefore not to be expected that derivatization of hirudin can be achieved without significant loss of activity. This expectation is distinctly verified by the work carried out by Walsmann (Pharmazie (1989), 44, 72) on the derivatization of the lysine residues of hirudin with dextran.

Because of the large number of acidic amino acids, conjugation of macromolecules with the carboxyl side-chains of hirudin is not expected to give a pure product. Even if only the basic functionalities of the polypeptide are derivatized, a mixture of up to 32 different compounds is expected. In the case of the mono-, di- and trisubstituted derivatives, a large number of positional isomers is conceivable, and these have substantially the same physical and chemical properties but differ an their biological activity. Even if the majority of the theoretically conceivable conjugates make contributions only in the trace range to the overall mixture, there must be expected to be considerable problems in the separation of an inhomogeneous product.

SUMMARY OF THE INVENTION

It has now been found that conjugation of poly-alkylene glycol derivatives can be so well controlled by using suitable hirudin muteins that chemically pure hirudin-polymer derivatives can be obtained with acceptable purification effort. It was surprising to find that hirudin/polyalkylene glycol derivatives of the general formula I

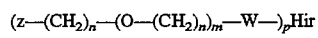

I in which z denotes one of the radicals —OH, —NH$_2$, —NH—CO—R, —O—R or —O—CO—R (with R meaning a C$_1$–C$_4$—alkyl [sic] group)

n denotes the number 2, 3 or 4 m denotes a number from 50 to 500

W denotes a direct covalent bond or a linker, p denotes the number 1, 2 or 3 and Hir denotes a hirudin residue which is bonded via the amino group(s) of the lysine side-chains to the

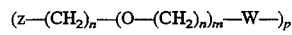

radicals, have distinctly prolonged bioavailabilities with the biological activity being wholly or substantially retained.

Suitable hirudin muteins are the following compounds and the salts thereof of the general formula II

```
          A—Tyr—Thr—Asp—Cys—Thr—Glu—Ser—Gly—     II
Gln—Asn—Leu—Cys—Leu—Cys—Glu—Gly—Ser—Asn—
    Val—Cys—Gly B—Gly—Asn—C —Cys—Ile—Leu—
D —Asn—Gln—Cys—Val—Thr—Gly—Glu—Gly—Thr—
     Pro—E —Pro—Gln—Ser—His—Asn—Asp—Gly—Asp—
          Phe—Glu—G —Ile—Pro—Glu—Glu—Tyr—Leu—F
```

(SEQ ID NO:1, SEQ ID NO:24, SEQ ID NO:25; SEQ ID NO:26 and SEQ ID NO:27.).
where
A=Val—Val
Ile—Thr
Leu—Thr
Pro—Val
B=Gln or Glu
C=Lys, Arg or Asn
D=—Lys—Gly— or
—Gly—U—V—Gly—X—Y— with
U=Ser, Lys or a direct bond
V=Asp, Lys or Asn
X=Glu, Gln or a direct bond
y=Lys, Arg or Asn
E=Lys, Arg, Asn or Gln
F=Asp or Gln
G=Glu or Pro.

BRIEF DESCRIPTION OF THE DRAWINGS

FIG. 2a. Synthetic DNA fragments 1A (SEQ ID NOS: 3 and 4), 2A (SEQ ID NOS: 5 and 6), 2B (SEQ ID NOS: 7 and 8), 2C (SEQ ID NOS: 9 and 10) and 2D (SEQ ID NOS: 11 and 12).

FIG. 2b. Synthetic DNA fragments 3A (SEQ ID NOS: 13 and 14), 3B (SEQ ID NOS: 15 and 16), 3C (SEQ ID NOS: 17 and 18).

DESCRIPTION OF THE PREFERRED EMBODIMENTS

Figure 1:
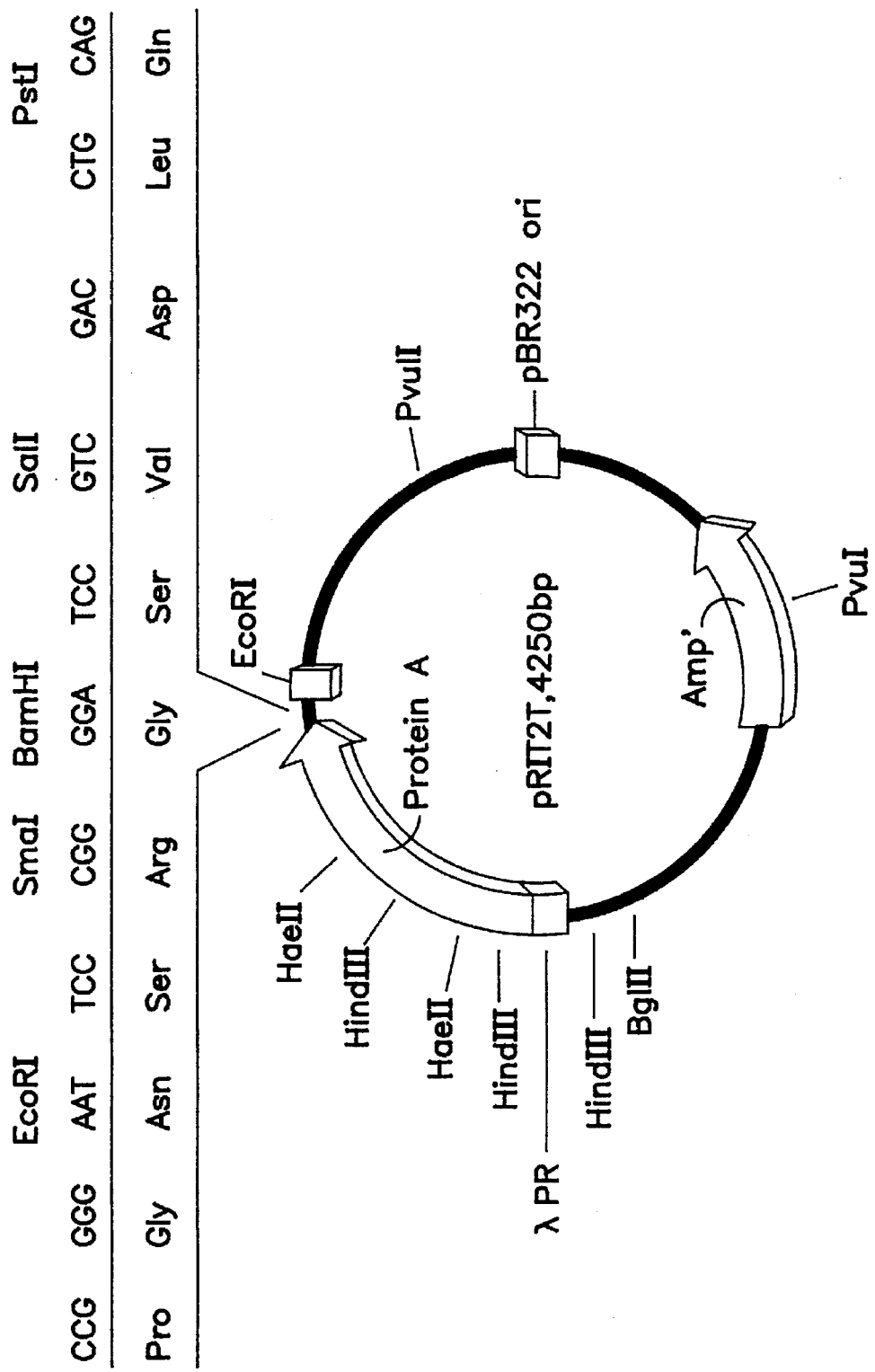
FIG. 1. Protein A vector pRIT 2T.

Muteins which have proven particularly suitable for conjugation with PEG are those in which the region between leucine 30 to glutamine 38 has been modified. It is possible to insert one or even two additional lysines in this region, and they then couple with simpler efficiency to that of the lysine residue 27. Furthermore, it is advantageous, in the interest of a simpler reaction procedure and of a chemically pure product, to replace lysine residues whose reaction with PEG is not wanted by other less nucleophilic amino acids. It has proven particularly beneficial in the abovementioned muteins to replace Lys 47 by Arg 47 or else Gln 47. The corresponding PEG-mutein coupling products have similarly high specific activities to those of the underivatized mutein. The proportion of the polymer capable of coupling, and thus the molecular weight of the conjugate, can be influenced by the number of lysine residues present or newly inserted.

Hirudin muteins of this type can very easily be prepared by genetic engineering means. First, the nucleic acid coding for the particular mutein is prepared by synthesis. These synthetic genes can then be provided with suitable regulatory sequences (promoter, terminator etc.) and be expressed in heterologous systems (FEBS-Lett. (1986) 202, 373 (1986); Biol. Chem. Hoppe-Seyler (1986) 367, 731). The expression can take place in eukaryotic systems (mammalian cells, yeasts or filamentous fungi) or in prokaryotic systems (*E. coli*, Bacilli etc.). Expression in *E. coli* preferably takes place via a fusion protein from which the hirudin can be liberated and subsequently activated (DNA (1986) 5, 511). In the examples which follow, the preparation of only some of the muteins claimed according to the invention is described by way of example, and the other muteins can be obtained analogously.

Suitable as linker B are the following groups:
—X—CO—; —X—CO—NH—W—NH—CO—; —X—CO—$CH_2$—$CH_2$—CO—; —X—$CH_2$—CO— or

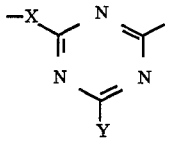

with

X meaning —S—, —O—, —NH— and

W meaning a $C_2$-$C_6$-alkylene group or a p-phenylene group and

Y meaning —Cl, —OH or H.

The novel hirudin/polyalkylene glycol derivatives can be prepared by reacting hirudin muteins of the general formula II with polyalkylene glycol derivatives of the general formula III $$A—(CH_2)_n—[O—(CH_2)_n]_m—E \qquad III$$

in which

A, m and n have the meaning already indicated, and

E [lacuna] one of the radicals —X—CO—Z, —X—CO—NH—W—N=C=O, —X—CO—$CH_2$—$CH_2$—CO—Z, —X—$CH_2$—CO—Z,

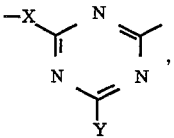

or —O—$SO_2$—R with X, W and Y in the indicated meaning and Z in the meaning of

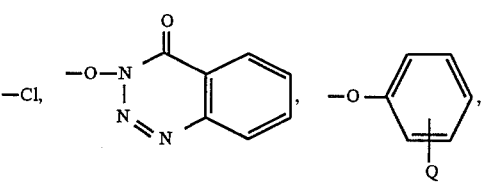

-continued

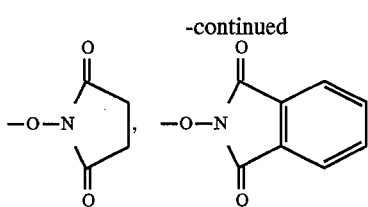

Q in the meaning of 1–3 halogen atoms or 1–2 nitro functionalities or an acetyl group and R in the meaning of methyl, ethyl, n-propyl, i-propyl, phenyl, tolyl or tresyl.

The reaction of II with hirudin muteins is carried out as follows: The activated polyalkylene glycol of the formula III is reacted in stoichiometric amounts or with an excess with hirudin, desulfatohirudin, a hirudin mutein in a suitable buffer (pH 6–10), in water, where appropriate with the addition of an auxiliary base such as sodium or potassium carbonate or bicarbonate, alkali metal hydroxide, triethylamine, N-methylmorpholine, diisopropylamine or pyridine in an organic solvent (methanol, ethanol, isopropanol, acetonitrile, dimethylformamide, N-methylpyrrolidone, dichloromethane, dimethyl sulfoxide, tetrahydrofuran, 1,4-dioxane, toluene) or in mixtures of the said solvents at temperatures between $-20°$ C. and $100°$ C., preferably at temperatures between $0°$ C. and $+60°$ C. The resulting conjugates are isolated and, using the methods customary in protein chemistry, purified and characterized.

The polyalkylene-hirudin conjugates described according to the invention have a pharmacological action profile which is more favorable than that of hirudin. They have not only the advantageous pharmacodynamic properties of hirudin but, furthermore, display a considerably prolonged biological activity and a better bioavailability. Furthermore, polyalkyl [sic] glycol/hirudin conjugates have a distinctly lower antigenicity than hirudin. By reason of these properties the polyalkylene conjugates described are superior to hirudin, heparin and low molecular weight heparin for the therapy and prophylaxis of thromboembolic disease. They can be used, for example, successfully for myocardial infarct, for deep vein thrombosis, peripheral arterial occlusive disease, pulmonary embolism and for extracorporeal circulation, for example hemodialysis or cardio-pulmonary bypass. Furthermore, the polyalkylene glycol/hirudin conjugates can be used to prevent reocclusion after reopening of arterial vessels by mechanical methods or lysis. In addition, the novel hirudin/polyalkylene glycol derivatives can be employed successfully for coating artificial surfaces such as, for example, hemodialysis membranes and the tubing systems necessary therefor, for vessel replacement or for heart-lung machines.

The compounds according to the invention can be administered orally or parenterally (subcutaneously, intravenously, intramuscularly, intraperitoneally) in a conventional way.

The dosage depends on the age, condition and weight of the patient and on the mode of administration. The daily dose of active substance is, as a rule, between about 20 to 40,000 ATU/kg of body weight, depending on the administration form and indication.

The novel compounds can be employed solid or liquid in the conventional pharmaceutical administration forms, for example as solutions, ointments, creams or sprays. These are produced in a conventional manner. The active substances can be processed for this purpose with the usual pharmaceutical auxiliaries such as fillers, preservatives, flow regulators, wetting agents, dispersants, emulsifiers, solvents and/or propellant gases (compare H. Sucker et al: Pharmazeutische Technologie, Thieme-Verlag, Stuttgart, 1978).

EXAMPLE 1

Preparation of the Hirudin Muteins a) Construction of the Vector

The protein A vector pRIT 2T (FIG. 1) is commercially available and described in detail (Pharmacia order No. 27-4808-01). It can be used to prepare peptides and proteins as fusion proteins with protein A from *Staphylococcus aureus* in *E. coli*. For this purpose the nucleic acid to be expressed must be inserted, retaining the protein A reading frame, into the polylinker of the vector pRIT 2T. The pRIT 2T DNA was cut with the restriction endonucleases Eco RI and Sal I in accordance with the manufacturer's instructions, the cleavage mixture was fractionated on a low-melting agarose gel, and the larger vector fragment was isolated from the gel in pure form. The fundamental techniques of genetic engineering and detailed working instructions are to be found in Sambrook et al. (1989) "Molecular Cloning" 2nd edition, CSH-Press. b) The sequences coding for the hirudin muteins claimed according to the invention were synthesized using an Applied Biosystems, model 380A DNA synthesizer in accordance with the instructions and using the chemicals from the manufacturer. The complete coding region was for this purpose assembled from 3 part-sequences to give in each case two complementary oligonucleotides. The oligonucleotides complementary to one another were mixed, heated at $90°$ C. for 5 minutes and cooled to room temperature over a period of 30 minutes. The double-stranded fragments resulting therefrom were kinased at their 5' ends and ligated together. It was possible to insert the hirudin gene formed in this way into the Eco RI and Sal I site of the linearized expression vector pRIT 2T in the correct orientation and retaining the protein A reading frame.

The following sequences (FIG. 2) were combined together to prepare the various muteins:

| Mutein | Combined sequences | Modification |
|---|---|---|
| Hirudin | 1A + 2A + 3A | — |
| HL 1 | 1A + 2A + 3B | Lys47→Arg47 |
| HL 11A | 1A + 2B + 3A | Ser32→Lys32 |
| | | Asp33→AsN33 |
| | | Glu35→GlN35 |
| HL 11B | 1A + 2B + 3B | Ser32→Lys32 |
| | | Asp33→AsN33 |
| | | Glu35→GlN35 |
| | | Lys47→Arg47 |
| HL 12A | 1A + 2C + 3A | Asp33→Lys33 |
| | | Glu35→GlN35 |
| HL 12B | 1A + 2C + 3B | Asp33→Lys33 |
| | | Glu35→GlN35 |
| | | Lys47→Arg47 |
| HL 14A | 1A + 2D + 3A | Asp33→Lys33 |
| | | Lys36→Arg36 |
| HL 14B | 1A + 2D + 3B | Asp33→Lys33 |
| | | Lys36→Arg36 |
| | | Lys47→Arg47 |
| HL 14C | 1A + 2D + 3C | Asp33→Lys33 |
| | | Lys36→Arg36 |
| | | Lys47→Gln47 |

The chimeric plasmids (pRIT 2T-Hir) resulting after the ligation are, for the DNA amplification, transformed into a lambda lysogenic strain, and DNA is isolated from single clones and examined by DNA sequence analysis for the presence of the correct sequence.

EXAMPLE 2

Expression of the Fusion Protein

The particular expression plasmid pRIT 2T-Hir was transformed into the strain *E. coli* N 4830-1 (Pharmacia order No.

27-4808-01). This strain contains chromosomally the thermosensitive lambda repressor CI 857.

100 ml of MIM medium (MIM=32 g of tryptone, 20 g of yeast extract, 6 g of $Na_2HPO_4$, 3 g of $KH_2PO_4$, 0.5 g of NaCl, 1 g of $NH_4Cl$ per liter and 0.1 mM $MgSO_4$, and 0.001 mM $FeCl_3$) were sterilized in a 1 l Erlenmeyer flask with baffles, and ampicillin (ad 100 μg/ml) was added. The medium was inoculated with 1 ml of a fresh overnight culture of the strain pRIT 2T-Hir/N 4830-1 and incubated with shaking at 28° C. until the absorption at 550 nm was 0.6. Then 100 ml of fresh MIM/amp medium at 65° C. were added, and incubation was continued at 42° C. for 4 h. The required fusion protein was synthesized in this time. The cell wall was removed enzymatically by adding lysozyme to 75 mg/l and incubating (3 h, 37° C.). It was then possible to disrupt the cells mechanically (Manton-Gaulin press, freezing cycle, vigorous stirring), by a heat shock at up to 80° C. or a hypotonic lysis, and to liberate the soluble fusion protein into the medium.

EXAMPLE 3

Purification of the Fusion Protein

The cell fragments were removed by centrifugation, and the clear supernatant was pumped through an IgG-Sepharose column (IgG-Sepharose® 6 "Fast Flow", Pharmacia, order No. 17-0969-01). The storage of the column material, preparation and setting up of the column, loading conditions and flow rates are as directed by the manufacturer's instructions. Thus, a 200 ml gel bed and a flow rate of about 3 l/h were used for 6 l of supernatant. In this step, the fusion protein was reversibly bound by its IgG-binding protein A part to the gel matrix (yield about 95%). After loading, the column was washed with 10 bed volumes of TST (50 mM tris-HCl pH 7.6; 150 mM NaCl and 0.05% Tween® 20). Elution was carried out with 0.5M acetate buffer pH 2.8.

EXAMPLE 4

Cleavage of the Fusion Protein

The column eluate from Example 3 was lyophilized and stored at −20° C. For cleavage, it was taken up in 70% strength formic acid to give a protein concentration of about 25 g/l. After flushing with argon, 1 g of solid BrCN was added per g of fusion protein to cleave off the hirudin. The cleavage was carried out under argon at 37° C. in about 4 h. The excess cyanogen bromide, the solvent and other volatile constituents were removed by lyophilization. Washing three times with water was then carried out.

EXAMPLE 5

Renaturation and Purification of Hirudin or Hirudin Muteins

The lyophilizate was taken up in 6M guanidine-HCl, 0.1M tris/HCl pH 8.5, 0.2M DTT to give 1–100 mg/ml protein. After an incubation time of 2 h, the sample was desalted by G-10 exclusion chromatography (equilibrated with 10 mM HCl). The desalted sample was diluted 1:20 in 0.1M tris/HCl, 5 mM GSH/0.5 mM GSSG, 1 mM EDTA, pH 8.7 and incubated for 1 h (GSH is reduced and GSSH [sic] is oxidized glutathione). This treatment resulted in the specific activity of the hirudin increasing by a factor of 3–5. After adjustment of the pH to pH 7.6 with HCl, addition of NaCl to 150 mM and Tween® 20 to 0.05%, the chromatography on IgG-Sepharose was repeated (Example 3).

Whereas the protein A fusion partner and uncleaved fusion protein were bound to the column, the active hirudin was present in a purity >90% in the flow-through. It was possible to purify it further to clinical purity by classical methods of protein chemistry.

EXAMPLE 6

Preparation of Methoxy-Polyethylene Glycol(8000) N-Succinimido Carbonate a) N-Succinimido Chloroformate 21.0 g of N-hydroxysuccinimide potassium salt are introduced over the course of 30 minutes into a solution of about 30 g of phosgene in 200 ml of dichloromethane at 0° C., and the mixture is stirred at 0° C. for 2 h. Subsequently, nitrogen is passed through the suspension for 1 h in order to blow out excess phosgene (NB absorber tower). The suspension is filtered, and the filtrate is evaporated to dryness in vacuo. The 10.6 g of N-succinimido chloroformate are in the form of a yellowish oil and are contaminated with inorganic salts and disuccinimido carbonate. The crude product can be employed without further purification for the reaction with polyalkylene glycols, or inorganic salts can be removed by dissolving in 150 ml of diethyl ether, filtering and evaporating again.

b) Methoxy-Polyethylene Glycol(8000) N-Succinimido Carbonate 10.0 g of methoxy-PEG(8000)—OH are dissolved in 20 ml of dry pyridine by warming gently. After cooling to room temperature, the solution is mixed with 890 mg of N-succinimido chloroformate and stirred overnight. After addition of an excess of diethyl ether, the mixture is stirred in an ice bath for 30 min, and the precipitated solid is filtered off, recrystallized twice from isopropanol, precipitated from diethyl ether, filtered and dried. 8.10 g of methoxy-polyethylene glycol(8000) N-succinimido carbonate result as a colorless solid.

EXAMPLE 7

Preparation of Methoxy-Polyethylene Glycol(8000) 4-Nitro-Phenyl Carbonate a) 4-Nitrophenyl Chloroformate About 43 g of phosgene are passed into a suspension of 20.0 g of nitrophenol in 60 ml of toluene at 0° C. The mixture is stirred at 0° C. for 4–5 h. Subsequently, at −15° C., a solution of 20 ml of triethylamine in 20 ml of toluene is slowly added dropwise, and the mixture is stirred in the thawing cold bath overnight. Excess phosgene is blown out with nitrogen, and the reaction mixture is subsequently filtered. The filtrate is evaporated to dryness in vacuo. The 33.7 g of oily brownish residue still contain solvent and salt in addition to 4-nitrophenol [sic] chloroformate. The mixture crystallizes in a refrigerator and can be employed without further purification.

b) Methoxy-Polyethylene Glycol(8000) 4-Nitrophenyl Carbonate

Preparation and purification in analogy to Example 6.

EXAMPLE 8

Preparation of Methoxy-Polyethylene Glycol(8000) 2,4,5-Trichlorophenyl Carbonate a) 2,4,5-Trichlorophenyl Chloroformate About 7 g of phosgene are passed into a solution of 10.0 g of 2,4,5-trichlorophenol in 50 ml of dichloromethane at 0°

C., and the mixture is stirred at 0° C. for 15 min. 7.2 ml of quinoline in 20 ml of dichloromethane are added dropwise over the course of 30 min, and the orange-colored suspension is then stirred in an ice bath for 1 h. Subsequently nitrogen is passed through the suspension for 1 h in order to blow out excess phosgene (absorber tower). The mixture is subsequently filtered, and the filtrate is washed twice with water, dried, again filtered and evaporated to dryness in vacuo. The 4.45 g of oily brownish residue are relatively pure 2,4,5-trichlorophenyl chloroformate, which crystallizes in the refrigerator and can be employed without further purification.

b) Methoxy-Polyethylene Glycol(8000) 2,4,5-trichlorophenyl Carbonate

Preparation and purification in analogy to Example 6.

EXAMPLE 9

Preparation of $PEG_1$-Hirudin by Reaction of Methoxy-Polyethylene Glycol(8000) 4-Nitrophenyl Carbonate with Hirudin 40 mg of desulfatohirudin (specific activity: 8,000 ATU/mg) are dissolved in 20 ml of 0.1M borate buffer, pH 8.0, and 80 mg of methoxy-polyethylene glycol(8000) 4-nitrophenyl carbonate are added and the mixture is incubated at 25° C. for 3 hours. The reaction is stopped with a 100-fold molar excess of tris base and then the reaction mixture is dialyzed against 20 mM tris/HCL [sic], pH 8.0, and the resulting product mixture is loaded onto an HP-Q-Sepharose® column (Pharmacia®). The column is developed with a linear NaCl gradient from 0 to 400 mM NaCl in 20 mM tris/HCl, pH 8.0. The $PEG_1$-hirudin conjugate elutes at 200 mM NaCl.

The yield of $PEG_1$ adduct in the coupling mixture is about 50%, and the remaining 50% of the hirudin is in the form of $PEG_2$ derivative or underivatized.

The specific activity of the $PEG_1$-hirudin conjugate purified from the coupling mixture was 8,000 U/mg of protein (determined by the thrombin inhibition assay with the chromogenic substrate S 2238 (Kabi), (FEBS-Lett. (1983), 164, 307), protein determined by BCA assay with serum albumin as standard (Pierce)), and the molecular weight of the conjugate was 15,000 Da (Superose®-12 chromatography, Pharmacia).

EXAMPLE 10

Preparation of $PEG_2$-Hirudin 40 mg of desulfatohirudin are dissolved in 10 ml of 0.05M sodium borate or sodium carbonate buffer, pH 8.0, and a solution of 240 mg of 2,4,5-trichlorophenyl- or 4-nitrophenyl-activated methoxypolyethylene glycol (8,000 Da) in $H_2O$ or 1,4 dioxane [sic] is added and incubated at 25° C. for 3 hours. The reaction is stopped with a 100-fold molar excess of tris base and then the reaction mixture is dialyzed against 20 mM tris/HCl, pH 8.0. The resulting product mixture is loaded onto an HP-Q-Sepharose® column, and the column is then developed with a linear NaCl gradient from 0 to 400 mM NaCl. The $PEG_2$-hirudin complex elutes at 120–130 mM NaCl.

The content of $PEG_2$-hirudin in the coupling mixture was about 50%, and the remainder of the hirudin was divided between PEG derivatives with 1 and 3 bonded PEG residues.

The specific activity of the purified $PEG_2$ conjugate was determined as described for Example 9 and was 6,200 U/mg of protein, and the molecular weight of the conjugate was 22,000 Da–23,000 Da (Superose®-12).

EXAMPLE 11

Reaction of the Hirudin Mutein HL 14B with Methoxy-Polyethylene Glycol(8000) 4-Nitrophenyl Carbonate 10 mg of the hirudin mutein HL 14B (specific activity 8,900 ATU/mg) were dissolved as in Example 10 to a concentration of 20 mg/ml in 0.1M sodium carbonate, buffer pH 8.0, 80 mg of 4-nitrophenyl-activated methoxy-polyethylene glycol (8,000 Da), dissolved in 0.5 ml of 1,4 dioxane [sic], were added, and the mixture was incubated at 25° C. for 3 hours. The reaction is then stopped by adding a 100-fold excess of tris base, liberated 4-nitrophenol is removed by extraction, and the hirudin-PEG conjugate is purified by anion exchange chromatography (see Example 9).

The content of the required $PEG_2$ derivative in the coupling mixture was about 80–85%; the content of unwanted $PEG_1$ and $PEG_3$ derivatives was in each case not more than about 5–10%. The specific activity of the purified $PEG_2$-HL 14B conjugate was 8,300 U/mg of protein. The molecular weight was determined by Superose® gel filtration to be 22,000–23,000 Da.

EXAMPLE 12

Pharmacokinetics of $PEG_2$-Hirudin Conjugates 2 groups of dogs (beagle dogs, 4 animals in each group) each received intravenous or subcutaneous administration of 4,000 U/kg $PEG_2$-hirudin (0.2 ml vol). 2 ml samples of blood in 0.1M Na citrate were taken 0.25, 0.5, 1, 2, 3, 4, 6, 8, 24, 32, 48, 56, 72 and 80 h after the injection. Subsequently platelet-poor plasma was prepared by centrifugation at 4,000 g for 10 minutes, and the plasma PEG-hirudin concentration was determined by the thrombin inhibition in the chromogenic substrate assay with S 2238 (Kabi). For comparison, the same dogs were treated in another experiment with hirudin. The time course of the plasma hirudin concentration was subsequently determined as described above.

Figure 3:
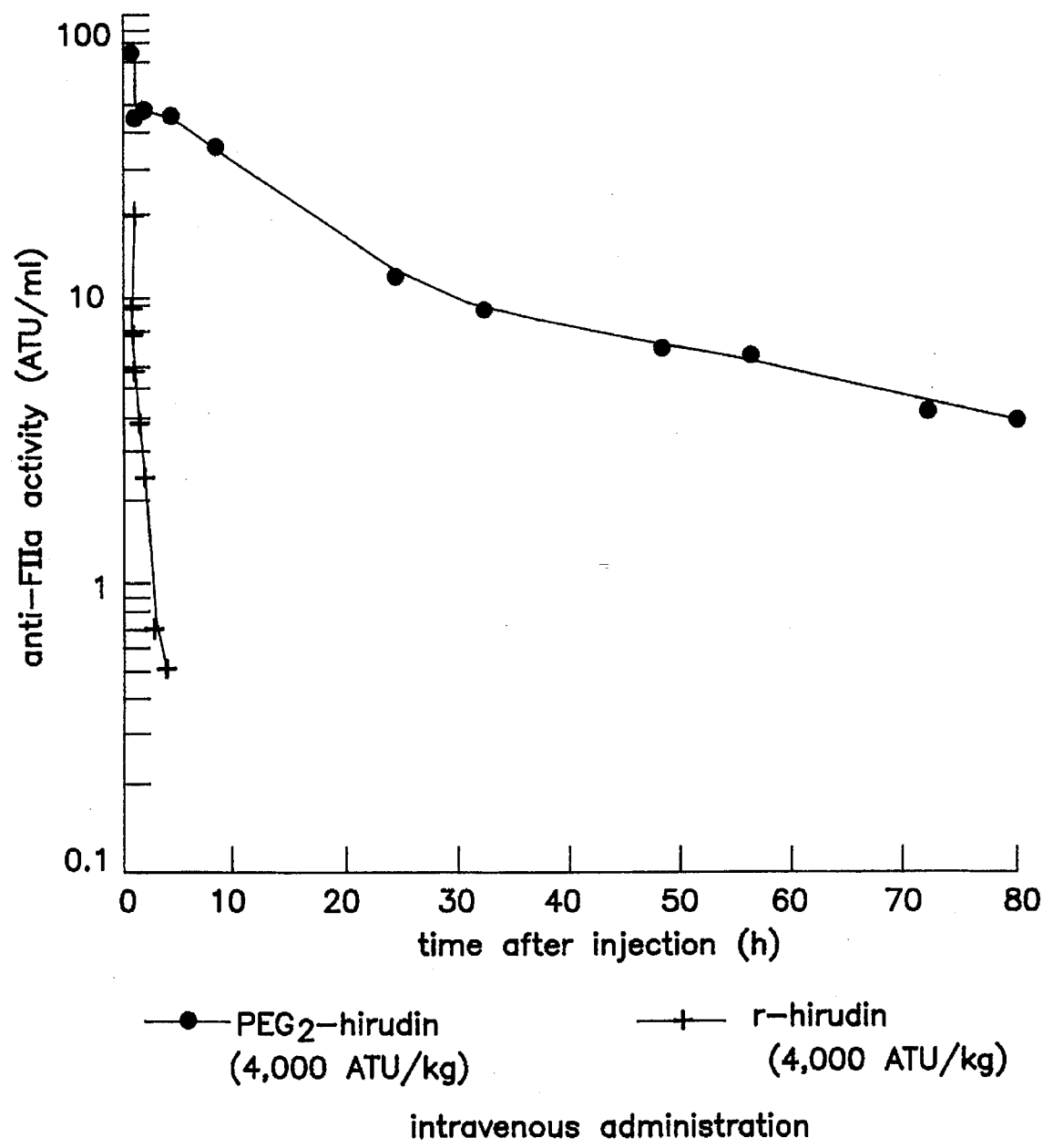
FIG. 3. Time course of anti-factor IIa activities after intravenous administration of $PEG_2$-hirudin and underivatized hirudin.
Figure 4:
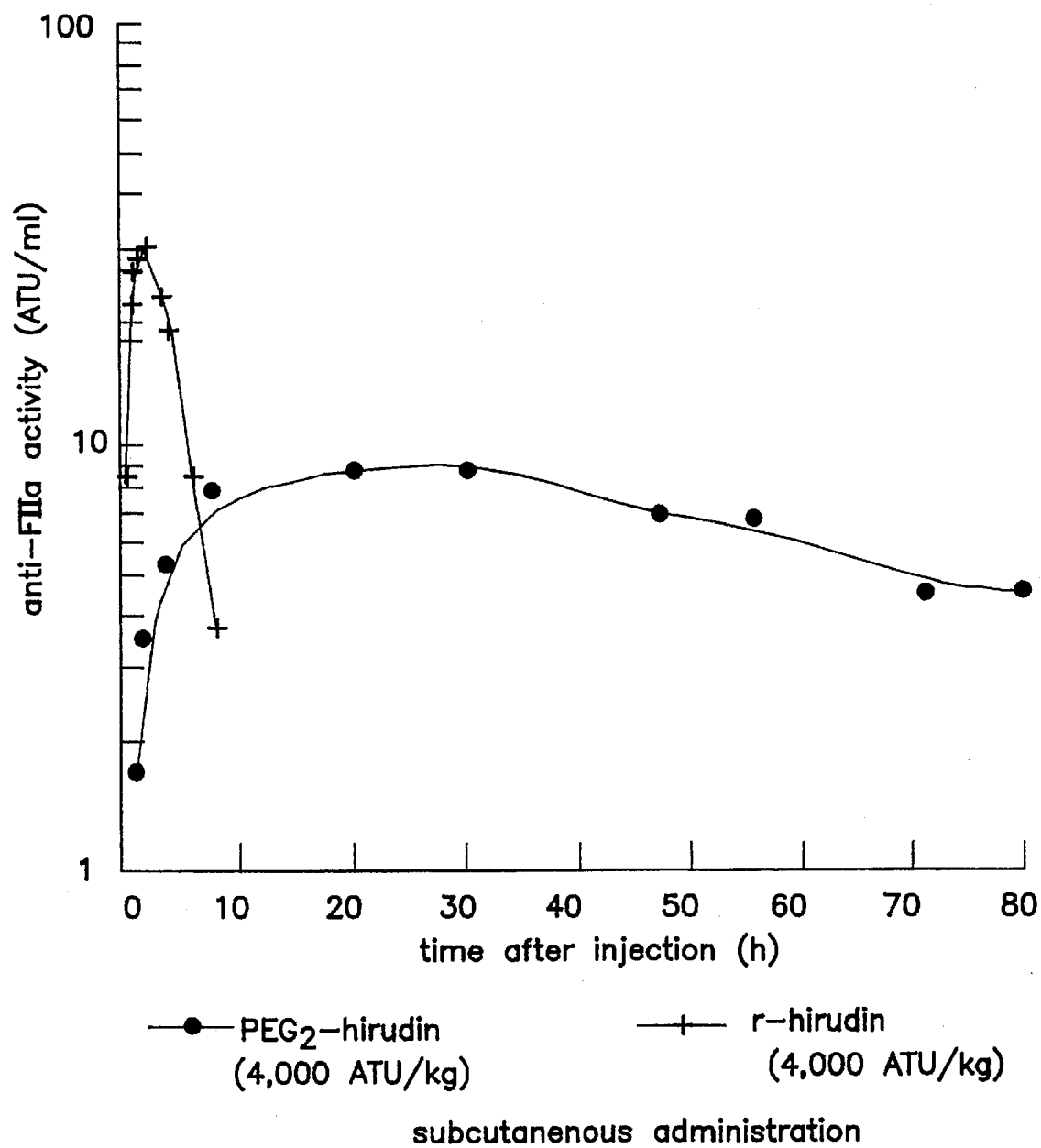
FIG. 4. Time course of anti-factor IIa activities after subcutaneous administration of $PEG_2$-hirudin and underivatized hirudin.

FIGS. 3 and 4 depict the time course of the anti-factor IIa activities after intravenous and subcutaneous administration of $PEG_2$-hirudin and underivatized hirudin. The distinctly prolonged duration of the biological action and the better bioavailability of the $PEG_2$-hirudin derivative are evident from the absolute values and the time course of the elimination plot.

We claim:

1. A hirudin mutein comprising an amino acid sequence represented by the following formula (SEQ. ID NO. 28):

Xaa—Xaa—Tyr—Thr—Asp—Cys—Thr—Glu—Ser—Gly—
10
Gln—Asn—Leu—Cys—Leu—Cys—Glu—Gly—Ser—Asn—
20
Val—Cys—Gly—Gln—Gly—Asn—Lys—Cys—Ile—Leu—
30
Gly—Ser—Lys—Gly—Glu—Arg—Asn—Gln—Cys—Val—
40
Thr—Gly—Glu—Gly—Thr—Pro—Arg—Pro—Gln—Ser—
50
His—Asn—Asp—Gly—Asp—Phe—Glu—Glu—Ile—Pro—
60
Glu—Glu—Tyr—Leu—Gln
65 wherein Xaa—Xaa at positions 1 and 2 in the amino acid sequence is Val—Val, Ile—Thr or Leu—Thr.

2. The hirudin mutein of claim 1, wherein Xaa—Xaa at positions 1 and 2 is Val—Val.

3. The hirudin mutein of claim 1, wherein Xaa—Xaa at positions 1 and 2 is Ile—Thr.

4. The hirudin mutein of claim 1, wherein Xaa—Xaa at positions 1 and 2 is Leu—Thr.

5. A conjugate of polyalkylene glycol or a polyalkylene glycol derivative with a hirudin mutein, said conjugate having the formula I

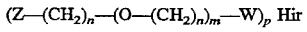
(Z—(CH$_2$)$_n$—(O—(CH$_2$)$_n$)$_m$—W)$_p$ Hir     I wherein,

Z is one of the radicals —OH, —NH—CO—R, —O—R or —O—CO—R, where R is a $C_1$-$C_4$-alkyl group;

n is 2, 3 or 4;

m is from 50 to 500;

W is a direct covalent bond or a linker;

p is 1, 2 or 3; and

Hir is the hirudin mutein defined in claim 1.

6. The conjugate of claim 5, wherein one or two polymer residues of the formula Z—(CH$_2$)$_n$—(O—(CH$_2$)$_n$)$_m$—W— are linked to the hirudin mutein.

7. The conjugate of claim 5, wherein the polyalkylene glycol is polyethylene glycol.

8. The conjugate of claim 9, wherein the molecular weight of the polyethylene glycol is between 4,000 and 15,000 daltons.

9. The conjugate of claim 5, wherein the hirudin mutein comprises a polypeptide represented by the following formula (SEQ ID NO: 22):

Val—Val—Tyr—Thr—Asp—Cys—Thr—Glu—Ser—Gly—
10
Gln—Asn—Leu—Cys—Leu—Cys—Glu—Gly—Ser—Asn—
20
Val—Cys—Gly—Gln—Gly—Asn—Lys—Cys—Ile—Leu—
30
Gly—Ser—Lys—Gly—Glu—Arg—Asn—Gln—Cys—Val—
40
Thr—Gly—Glu—Gly—Thr—Pro—Arg—Pro—Gln—Ser—
50
His—Asn—Asp—Gly—Asp—Phe—Glu—Glu—Ile—Pro—
60
Glu—Glu—Tyr—Leu—Gln.
65

10. A method for treating a host in need of thrombin-inhibiting activity, which comprises administering to said host an effective amount of the conjugate of claim 5.

11. The method of claim 10, wherein the host is suffering from myocardial infarction, deep vein thrombosis, peripheral arterial occlusive disease or pulmonary embolism.

12. The method of claim 10, wherein Xaa—Xaa at positions 1 and 2 in the hirudin mutein is Val—Val.

13. A method for preventing the coagulation of blood on a surface of an article, which comprises coating said surface with the conjugate of claim 5.

14. The method of claim 13, wherein Xaa—Xaa at positions 1 and 2 in the hirudin mutein is Val—Val.

15. A method for preventing the coagulation of blood on a surface of an article, which comprises coating said surface with the hirudin mutein of claim 1.

* * * * *